United States Patent [19]

Wada et al.

[11] Patent Number: 4,946,495

[45] Date of Patent: * Aug. 7, 1990

[54] 2-PHENOXYPYRIMIDINE DERIVATIVE AND HERBICIDAL COMPOSITION

[75] Inventors: Nobuhide Wada; Yoshihiro Saito, both of Shizuoka; Shoji Kusano, Hamamatsu; Yasufumi Toyokawa, Shizuoka; Takeshige Miyazawa, Shizuoka; Satoru Takahashi, Shizuoka; Takayoshi Takehi, Shizuoka, all of Japan

[73] Assignees: Kumiai Chemical Industry Co., Ltd.; Ihara Chemical Industry Co., Ltd., both of Tokyo, Japan

[*] Notice: The portion of the term of this patent subsequent to Dec. 26, 2006 has been disclaimed.

[21] Appl. No.: 181,319

[22] Filed: Apr. 13, 1988

[30] Foreign Application Priority Data

Apr. 14, 1987 [JP] Japan .................. 62-091783
Apr. 14, 1987 [JP] Japan .................. 62-091786
Dec. 5, 1987 [JP] Japan .................. 62-308283
Dec. 28, 1987 [JP] Japan .................. 62-336251

[51] Int. Cl.$^5$ ............... A01N 43/54; C07D 239/52
[52] U.S. Cl. .................. 71/92; 544/229; 544/299; 544/300; 544/301; 544/302; 544/303; 544/309; 544/310; 544/313; 544/314
[58] Field of Search ............... 544/229, 299, 300, 301, 544/302, 303, 309, 310, 313, 314; 71/92

[56] References Cited

U.S. PATENT DOCUMENTS

4,427,437 1/1984 Serban et al. .................. 544/299
4,770,691 9/1988 Nezu et al. .................... 544/310

FOREIGN PATENT DOCUMENTS

001187 3/1979 European Pat. Off. .
15124 9/1980 European Pat. Off. .......... 544/316
256985 2/1988 European Pat. Off. .......... 544/316
3602016 6/1987 Fed. Rep. of Germany ...... 544/316
9474 5/1967 Japan .
55729 5/1979 Japan .
117486 9/1979 Japan .
7046968 3/1982 Japan .................. 544/316

OTHER PUBLICATIONS

Serban et al, Chem. Abst. 92-175773f (1980), "Certain Pyrimidine Derivatives for Inhibiting the Growth of Plants".
Kijima et al, Chem. Abst. 93-150268c (1980), "2-Phenoxy Pyrimidine Derivatives".
Nezu et al, Chem. Abst. 107-134322t (1987).
Saito et al, Chem. Abst. 108-167496b (1988).
Shigematsu et al, Chem. Abst. 108-167509h (1988).
Agr. Biol. Chem., vol. 30, No. 9, pp. 896-905, 1966, Jojima et al, "Syntheses and Herbicidal Activities of . . . ".

Primary Examiner—Cecilia Shen
Attorney, Agent, or Firm—Oblon, Spivak, McClelland, Maier & Neustadt

[57] ABSTRACT

A 2-phenoxypyrimidine derivative having the formula:

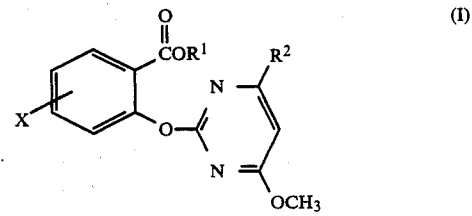

(I)

wherein X is a halogen atom or

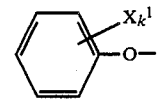

wherein $X^1$ is a halogen atom, a lower alkyl group or a lower alkoxy group and k is 0, 1 or 2; $R^1$ is a hydrogen atom, a benzyl group, —$(CH_2)_mR^3$ wherein $R^3$ is a cyano group, a formyl group, a dialkylamino group, a phenyl group, a pyridyl group, a trimethylsilyl group, a naphthyl group, an alkoxycarbonyl group, a benzoyl group, an alkylthio group, a phenylthio group, an alkylsulfonyl group or a benzyloxy group and m is 1, 2 or 3, or

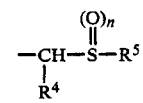

wherein $R^4$ is a hydrogen atom or a lower alkyl group, $R^5$ is a lower alkyl group or

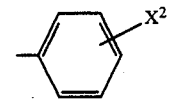

wherein $X^2$ is a hydrogen atom, a halogen atom, a lower alkyl group, a lower alkoxy group or a nitro group, n is 0 or 1, provided that when $R^5$ is an alkyl group, n is 1; and $R^2$ is a chlorine atom or a methoxy group, provided that when $R^1$ is a hydrogen atom or a benzyl group, X is

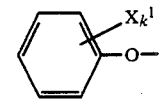

and $R^2$ is a methoxy group, when $R^1$ is (Abstract continued on next page.)

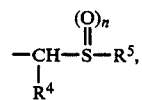
X is a chlorine atom at the 6-position and $R^2$ is a methoxy group, and when $R^1$ is $-(CH_2)_mR^3$, X is a halogen atom at the 6-position.
11 Claims, No Drawings

2-PHENOXYPYRIMIDINE DERIVATIVE AND HERBICIDAL COMPOSITION

The present invention relates to novel 2-phenoxypyrimidine derivatives and herbicidal compositions containing them as active ingredients, which are applicable to paddy rice fields, upland fields and non-agricultural fields.

It is disclosed that some 2-phenoxypyrimidine derivatives have herbicidal activities, for instance, in (1) A gr. Biol. Chem. Vol. 30, No. 9, p. 896 (1966), (2) Japanese Unexamined Patent Publication No. 55729/1979 (U.S. Pat. No. 4,427,437), (3) Japanese Unexamined Patent Publication No. 117486/1979 and (4) Japanese Examined Patent Publication No. 9474/1967.

However, the compounds disclosed in such publications and literature have no adequate herbicidal effects against annual weeds, and they exhibit no substantial herbicidal activities against perennial weeds.

The present inventors have conducted extensive research on 2-phenoxypyrimidine compounds with an aim to develop a compound having excellent herbicidal activities and have previously reported some compounds in E.P. No. 223,406A, 249,707A and 249,708A. As a result of further research, they have now found that the compounds of the present invention with substituents introduced to certain specific positions on the pyrimidine and benzene rings exhibit excellent herbicidal effects not only against annual weeds but also against perennial weeds, particularly against purple nutsedge (*Cyperus rotundus*) and Johnsongrass (*Sorghun halepense*), and at the same time they have a high level of safety against crop plants. The present invention has been accomplished on the basis of these discoveries.

The present invention provides a 2-phenoxypyrimidine derivative having the formula:

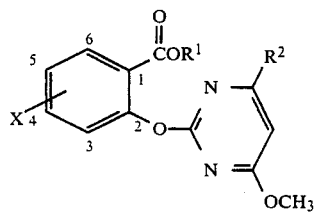  (I)

wherein X is a halogen atom or

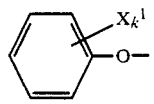

wherein $X^1$ is a halogen atom, a lower alkyl group (preferably a $C_1$-$C_5$ alkyl group), a nitro group or an alkylthio group (preferably a $C_1$-$C_5$ alkylthio group), a lower alkoxy group (preferably a $C_1$-$C_5$ alkoxy group) and k is 0, 1 or 2; $R^1$ is a hydrogen atom, a benzyl group, —$(CH_2)_m R^3$ wherein $R^3$ is a cyano group, a formyl group, a dialkylamino group (preferably a di-$C_1$-$C_5$ alkylamino group), a phenyl group, a pyridyl group, a trimethylsilyl group, a naphthyl group, an alkoxycarbonyl group (preferably a $C_1$-$C_5$ alkoxycarbonyl group), a benzoyl group, an alkylthio group (preferably a $C_1$-$C_5$ alkylthio group), a phenylthio group, an alkylsulfonyl group (preferably $C_1$-$C_5$ alkylsulfonyl group) or a benzyloxy group and m is 1, 2 or 3, or

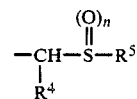

wherein $R^4$ is a hydrogen atom or a lower alkyl group (preferably a $C_1$-$C_5$ alkyl group), $R^5$ is a lower alkyl group (preferably a $C_1$-$C_5$ alkyl group) or

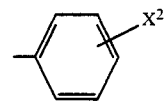

wherein $X_2$ is a hydrogen atom, a halogen atom, a lower alkyl group (preferably a $C_1$-$C_5$ alkyl group), a lower alkoxy group (preferably a $C_1$-$C_5$ alkoxy group) or a nitro group, n is 0 or 1, provided that when $R^5$ is an alkyl group, n is 1; and $R^2$ is a chlorine atom or a methoxy group, provided th $R^1$ is a hydrogen atom or a benzyl group, X is

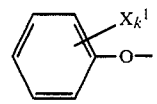

and $R^2$ is a methoxy group, when $R^1$ is

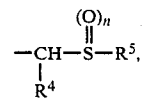

X is a chlorine atom at the 6-position and $R^2$ is a methoxy group, and when $R^1$ is —$(CH_2)_m R^3$, X is a halogen atom at the 6-position.

The present invention also provides a 2-phenoxypyrimidine derivative having the formula:

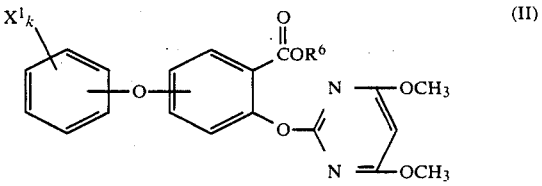  (II)

wherein $X^1$ is a halogen atom, a lower alkyl group (preferably a $C_1$-$C_5$ alkyl group) or a lower alkoxy group (preferably a $C_1$-$C_5$ alkoxy group), k is 0, 1 or 2, and $R^6$ is a hydrogen atom or a benzyl group.

Further, the present invention provides a herbicidal composition which comprises a herbicidally effective amount of a 2-phenoxypyrimidine derivative of the formula I or II and an agricultural carrier.

Now, the present invention will be described in detail with reference to the preferred embodiments.

A preferred group of the compounds of the present invention may be represented by the formula:

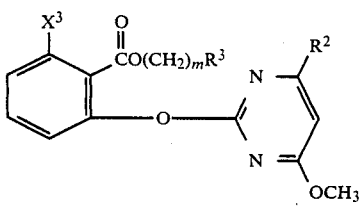

(III)

wherein $R^3$ is a cyano group, a formyl group, a dialkylamino group, a phenyl group, a pyridyl group, a trimethylsilyl group, a naphthyl group, an alkoxycarbonyl group, a benzoyl group, an alkylthio group, a phenylthio group, an alkylsulfonyl group or a benzyloxy group, $R^2$ is a chlorine atom or a methoxy group, $X^3$ is a halogen atom, and m is 1, 2 or 3.

Another preferred group of the compounds of the present invention may be represented by the formula:

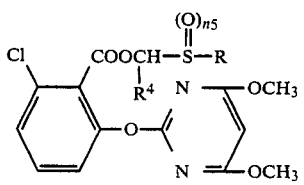

(IV)

wherein $R^4$ is a hydrogen atom or a lower alkyl group (preferably a $C_1$-$C_5$ alkyl group), $R^5$ is a lower alkyl group (preferably a $C_1$-$C_5$ alkyl group) or

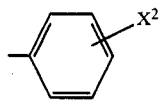

wherein $X^2$ is a halogen atom, a lower alkyl group (preferably a $C_1$-$C_5$ alkyl group), a lower alkoxy group (preferably a $C_1$-$C_5$ lower alkoxy group) or a nitro group, and n is 0 or 1, provided that when $R^5$ is an alkyl group (preferably a $C_1$-$C_5$ alkyl group), n is 1.

In a preferred embodiment, $X^1$ is a methyl group, a methoxy group or a halogen atom, and k is 1 or 2.

The phenoxy group is substituted preferably at the 5-position or the 6-position, more preferably at the 6-position.

$R^2$ is preferably a methoxy group. $R^3$ is preferably a benzoyl group, a benzyloxy group, an alkylthio group, an alkoxycarbonyl group, a phenylthio group, an alkylsulfonyl group or a cyano group, more preferably a benzyloxy group, an alkylthio group, a phenylthio group or an alkylsulfonyl group, most preferably a benzyloxy group, a phenylthio group, a methylsulfonyl group or a methylthio group, and m is 1. In another preferred embodiment, n is 0 and $R^5$ is

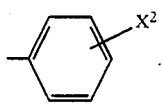

Now, specific examples of the compound of the present invention will be presented in Tables 1 to 3. Compound numbers given in these Tables will be referred to in the subsequent description in the specification.

TABLE 1

(III)

| Compound No. | $R^3$ | $R^2$ | X | m | Melting point (°C.) or refractive index $n_D^{20}$ |
|---|---|---|---|---|---|
| 1 | CO—⟨phenyl⟩ | Cl | F | 1 | 1.5834 |
| 2 | CO—⟨phenyl⟩ | $OCH_3$ | F | 1 | 110–112 |
| 3 | $Si(CH_3)_3$ | $OCH_3$ | F | 2 | 1.5159 |
| 4 | $OCH_2$—⟨phenyl⟩ | $OCH_3$ | F | 1 | 1.5582 |
| 5 | $SCH_3$ | $OCH_3$ | Cl | 1 | 1.5575 |
| 6 | $CO_2CH_3$ | $OCH_3$ | Cl | 1 | 1.5350 |
| 7 | CO—⟨phenyl⟩ | $OCH_3$ | Cl | 1 | 99–102 |
| 8 | —S—⟨phenyl⟩ | $OCH_3$ | Cl | 1 | 73–75 |
| 9 | $SO_2CH_3$ | $OCH_3$ | Cl | 1 | 95–97 |
| 10 | CN | $OCH_3$ | Cl | 1 | 1.5442 |
| 11 | ⟨naphthyl⟩ | $OCH_3$ | Cl | 1 | 99–104 |
| 12 | CHO | $OCH_3$ | Cl | 2 | 1.5425 |
| 13 | $N(CH_3)_2$ | $OCH_3$ | Cl | 2 | 1.5422 |
| 14 | $SC_2H_5$ | $OCH_3$ | Cl | 2 | 1.5510 |
| 15 | ⟨phenyl⟩ | $OCH_3$ | Cl | 2 | 101–104 |
| 16 | ⟨phenyl⟩ | $OCH_3$ | Cl | 3 | 1.5602 |

TABLE 1-continued

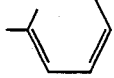

(III)

| Compound No. | R³ | R² | X | m | Melting point (°C.) or refractive index $n_D^{20}$ |
|---|---|---|---|---|---|
| 17 | 2-pyridyl | OCH₃ | Cl | 1 | 1.5707 |

TABLE 2

(II)

| Compound No. | R⁶ | Substituted position | $X_k^1$ | Melting point (°C.) or refractive index $n_D^{20}$ |
|---|---|---|---|---|
| 2-1 | H | 5 | H | 142–144 |
| 2-2 | CH₂-phenyl | 6 | H | 1.5869 |
| 2-3 | H | 6 | H | 116–118 |
| 2-4 | CH₂-phenyl | 6 | 4-Cl | 1.5920 |
| 2-5 | CH₂-phenyl | 6 | 2-CH₃ | 1.5807 |
| 2-6 | CH₂-phenyl | 6 | 3-CH₃ | 91–93 |
| 2-7 | CH₂-phenyl | 6 | 4-CH₃ | 1.5839 |
| 2-8 | H | 6 | 2-CH₃ | 126–127 |
| 2-9 | H | 6 | 3-CH₃ | 139–141 |
| 2-10 | H | 6 | 4-CH₃ | 139–141 |
| 2-11 | H | 6 | 3,5-(CH₃)₂ | 127–129 |
| 2-12 | CH₂-phenyl | 6 | 3,5-(CH₃)₂ | 69–73 |
| 2-13 | H | 6 | 3,5-(OCH₃)₂ | 132–134 |
| 2-14 | CH₂-phenyl | 6 | 2-OCH₃ | 1.5853 |
| 2-15 | H | 6 | 2-OCH₃ | 151–154 |
| 2-16 | H | 6 | 2-C₃H₇-i | 133–134 |
| 2-17 | CH₂-phenyl | 6 | 2-C₃H₇-i | 1.5720 |
| 2-18 | H | 6 | 2-Cl | 130–132 |
| 2-19 | H | 6 | 2-F | 134–135 |
| 2-20 | H | 6 | 3-Cl | 136–137 |
| 2-21 | H | 6 | 2-C₂H₅ | 125–127 |
| 2-22 | H | 6 | 2,6-(CH₃)₂ | 153–155 |
| 2-23 | H | 6 | 2,3-(CH₃)₂ | 143–145 |
| 2-24 | H | 6 | 2,4-(CH₃)₂ | 135–136 |
| 2-25 | H | 6 | 2,5-(CH₃)₂ | 126–128 |
| 2-26 | H | 6 | 3,4-(CH₃)₂ | 142–144 |
| 2-27 | H | 6 | 3-F | 116–117 |
| 2-28 | H | 6 | 4-F | 130–131 |
| 2-29 | CH₂-phenyl | 6 | 3,5-(OCH₃)₂ | 1.5786 |
| 2-30 | H | 6 | 3-OCH₃ | 112–115 |
| 2-31 | H | 6 | 4-OCH₃ | 132–235 |
| 2-32 | H | 6 | 3-Br | 148–149 |
| 2-33 | H | 6 | 4-Br | 132–135 |
| 2-34 | H | 6 | 3-OC₂H₅ | 105–107 |
| 2-35 | H | 6 | 2-Br | 131–133 |
| 2-36 | H | 6 | 4-OC₂H₅ | 133–134 |
| 2-37 | H | 6 | 2-OC₂H₅ | 129–131 |
| 2-38 | H | 6 | 2,4-F₂ | 136–139 |
| 2-39 | H | 6 | 3,4-F₂ | 130–133 |
| 2-40 | H | 6 | 2,4-Cl₂ | 154–157 |
| 2-41 | H | 6 | 4-Cl | 131–133 |
| 2-42 | H | 6 | 2-NO₂ | 155–157° C. |
| 2-43 | H | 6 | 4-SCH₃ | 149–151° C. |
| 2-44 | H | 6 | 2-SCH₃ | 150–153° C. |

TABLE 3

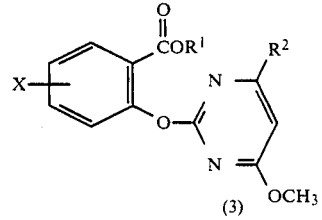

| Compound No. | R⁴ | R⁵ | n | Melting point (°C.) or refractive index $n_D^{20}$ |
|---|---|---|---|---|
| 3-1 | H | $CH_3$ | 1 | 1.5627 |
| 3-2 | $CH_3$ | phenyl | 0 | 1.5812 |
| 3-3 | H | o-tolyl ($CH_3$) | 0 | 77–82 |
| 3-4 | H | m-tolyl ($CH_3$) | 0 | 1.5923 |
| 3-5 | H | p-tolyl ($CH_3$) | 0 | 1.5925 |
| 3-6 | H | p-chlorophenyl (Cl) | 0 | 1.6019 |
| 3-7 | H | p-methoxyphenyl ($OCH_3$) | 0 | 1.5949 |
| 3-8 | H | p-nitrophenyl ($NO_2$) | 0 | 120–123 |

The compounds of the present invention can be produced by the following processes, but their production is not restricted to such specific processes.

PROCESS A

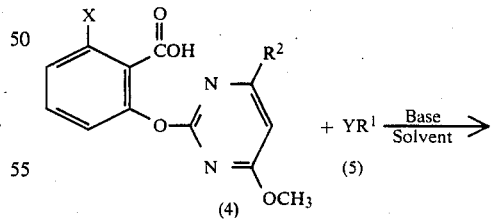

In the above formulas, $R^7$ is a halogen atom, an alkylsulfonyl group, a benzylsulfonyl group or a substituted benzylsulfonyl group, and $R^1$, $R^2$ and X are as defined above.

Among the compounds of the present invention, those represented by the formula 3 can be prepared by reacting the phenol compound of the formula 1 and a pyrimidine compound of the formula 2 in the presence of a base, preferably in a solvent, within a temperature range from room temperature to the boiling point of the solvent, for from 1 to 24 hours. When the reaction is conducted in the absence of a solvent, the reaction can be conducted within a temperature range from 120° to 160° C. by using a carbonate of an alkali metal, such as anhydrous potassium carbonate.

Here, as the solvent, there may be employed a hydrocarbon solvent such as benzene, toluene or xylene, a halogenated hydrocarbon solvent such as dichloromethane or chloroform, an alcohol solvent such as methanol, ethanol or isopropanol, an ether solvent such as ethyl ether, isopropyl ether, tetrahydrofuran or 1,4-dioxane, a ketone solvent such as acetone or methyl ethyl ketone, an ester solvent such as methyl acetate or ethyl acetate, an aprotic polar solvent such as dimethylformamide, dimethylacetamide or dimethylsulfoxide, and others such as acetonitrile or water.

As the base, there may be employed an alkali metal such as sodium metal or potassium metal, an alkali metal or alkaline earth metal hydride such as sodium hydride, potassium hydride or calcium hydride, a carbonate such as sodium carbonate or potassium carbonate, or a metal hydroxide such as sodium hydroxide or potassium hydroxide.

PROCESS B

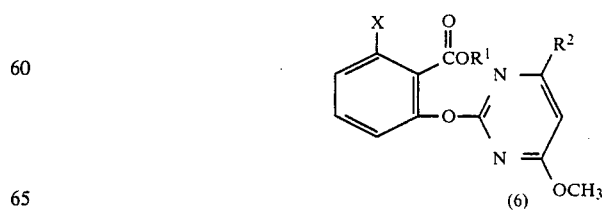

In the above formulas, Y is a halogen atom, an alkylsulfonyloxy group, a benzenesulfonyloxy group or a substituted benzenesulfonyloxy group, $R^1$ is —$(CH_2)_mR^3$, or

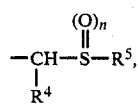

and $R^2$, $R^3$, $R^4$, $R^5$, X and n are as defined above.

Among the compounds of the present invention, the compounds of the formula 6 can be prepared by reacting the compound of the formula 4 with the compound of the formula 5 in the presence of a base preferably in a solvent within a temperature range of from room temperature to the boiling point of the solvent for from 1 to 24 hours.

Here, the solvent may be a hydrocarbon solvent such as benzene, toluene or xylene, a halogenated hydrocarbon solvent such as dichloromethane or chloroform, an ether solvent such as ethyl ether, isopropyl ether, tetrahydrofuran or 1,4-dioxane, a ketone solvent such as acetone or methyl ethyl ketone, an ester solvent such as methyl acetate or ethyl acetate, an aprotic polar solvent such as dimethylformamide, dimethylacetamide or dimethylsulfoxide, acetonitrile or water.

The base may be an alkali metal such as sodium metal or potassium metal, an alkali metal hydride or an alkaline earth metal hydride such as sodium hydride, potassium hydride or calcium hydride, a carbonate such as sodium carbonate, potassium carbonate, sodium hydrogencarbonate or potassium hydrogencarbonate, a metal hydroxide such as sodium hydroxide or potassium hydroxide or an organic base such as trialkylamine (a tertiary amine) or pyridine.

PROCESS C

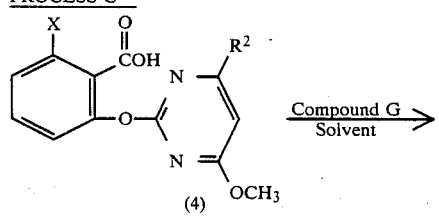

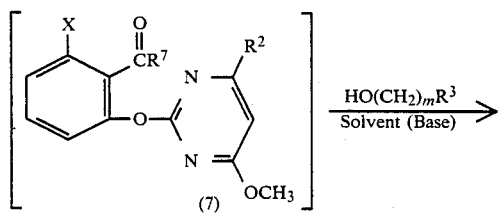

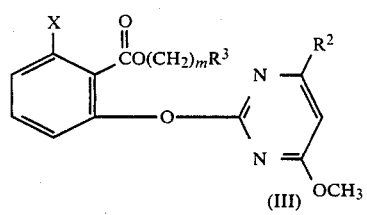

In the above formulas, $R^7$ is an imidazolyl group or a chlorine atom, and $R^3$, $R^2$, X and m are as defined above.

Among the compounds of the present invention, those represented by the formula III can be prepared by reacting the compound of the formula 4 with the compound G in a solvent within a temperature range of from room temperature to the boiling point of the solvent for from 1 to 12 hours to obtain a compound of the formula 7 and then reacting the compound of the formula 7 in a solvent, if necessary in the presence of a base within a temperature range of from cooling with ice to room temperature, if necessary at the boiling point of the solvent, for from 0.5 to 12 hours.

Here, the compound G may be carbonyldiimidazole, thionyl chloride, oxalic acid dichloride or phosgene.

The solvent used for the reactions from the formula 4 to formula 7 and from the formula 7 to formula III may be a hydrocarbon solvent such as benzene, toluene or xylene, a halogenated hydrocarbon solvent such as dichloromethane or chloroform, an ether solvent such as ethyl ether, isopropyl ether, tetrahydrofuran or 1,4-dioxane, a ketone solvent such as acetone or methyl ethyl ketone, an ester solvent such as methyl acetate or ethyl acetate. The base used for the reaction from the formula 7 to the formula III may be selected from organic amines and inorganic bases.

PROCESS D

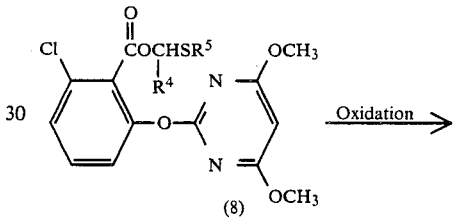

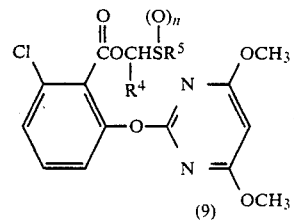

In the above formulas, $R^4$, $R^5$ and n are as defined above.

The compounds of the formula IV of the present invention can be produced also by oxidizing the compound of the formula 8.

As the oxydizing agent, a peroxide such as hydrogen peroxide, peracetic acid, perbenzoic acid or m-chloroperbenzoic acid, sodium metaperiodate, ozone, hydroperoxide or potassium peroxysulfate may be employed. The production can be conducted in accordance with a usual method for the preparation of a sulfoxide.

PROCESS E

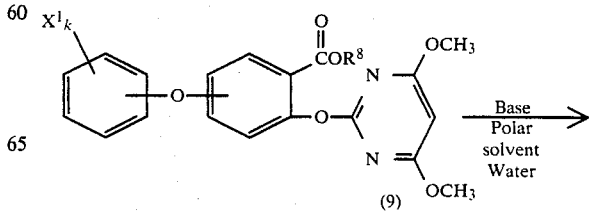

PROCESS E

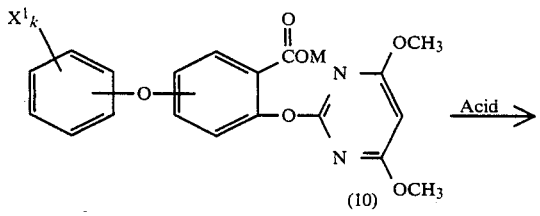

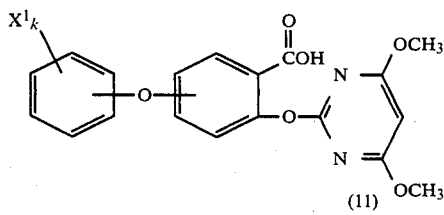

In the above formulas, $R^8$ is a lower alkyl group, a 2-(trimethylsilyl)ethyl group or a benzyl group, M is an alkali metal or an alkaline earth metal, and $X^1$, k are as defined above.

The compound of the formula 11 of the present invention can be produced by reacting the compound of the formula 9 in the presence of a base in a polar solvent, in water or in a solvent mixture of a polar solvent and water within a temperature range of from room temperature to the boiling point of the solvent for from 0.5 to 36 hours to obtain a compound of the formula 10, and then treating this compound with an acid for precipitation.

The solvent to be used here may be an alcohol solvent such as methanol, ethanol or isopropanol, or a ketone solvent such as acetone or methyl ethyl ketone. The base may be a carbonate such as sodium carbonate, potassium carbonate, calcium carbonate, sodium hydrogen carbonate or potassium hydrogen carbonate, or a metal hydroxide such as sodium hydroxide or potassium hydroxide.

Further, when $R^8$ in the formula 9 is a benzyl group, the compound of the formula 11 may be produced by catalytic reduction with hydrogen.

Furthermore, when $R^2$ in the formula 9 is a 2-(trimethylsilyl)ethyl group, the compound of the formula 11 may be prepared by the reaction with tetra-n-butyl ammoniumfluoride.

Now, the present invention will be described in further detail with reference to Examples. However, it should be understood that the present invention is by no means restricted to such specific Examples.

EXAMPLE 1

Preparation of 2-(trimethylsilyl)ethyl 6-(4,6-dimethoxypyrimidin-2-yl)oxy-2-fluorobenzoate (Compound No. 3)

6-(4,6-dimethoxypyrimidin-2-yl)oxy-2-fluorobenzoic acid (3.0 g) and carbonyldiimidazole (1.8 g) were dissolved in 50 ml of tetrahydrofuran, and the mixture was refluxed under heating and stirring for one hour. After cooling the reaction solution, 2-(trimethylsilyl)ethanol (6.0 g) and potassium carbonate (1.5 g) were added thereto, and the mixture was refluxed under heating and stirring for one hour. The reaction solution was poured into ice water and extracted with ethyl ether. The extract was washed with water and dried. Then, the solvent was evaporated under reduced pressure. The residue thereby obtained was purified by silica gel column chromatography to obtain the above identified compound as a pale yellow oily substance (2.4 g). Refractive index $n_D^{20}$: 1.5159.

EXAMPLE 2

Preparation of cyanomethyl 2-chloro-6-(4,6-dimethoxypyrimidin-2-yl)oxy benzoate (Compound No. 10)

2-chloro-6-(4,6-dimethoxypyrimidin-2-yl)oxy benzoic acid (1.6 g), chloro acetonitrile (0.6 g) and potassium carbonate (0.9 g) were suspended in dimethylformamide (10 ml), and the suspension was heated and stirred at a temperature of from 80° to 90° C. for one hour. The reaction solution was poured into water and extracted with ethyl acetate. The extract was washed with water and dried. Then, the solvent was evaporated under reduced pressure. The residue thereby obtained was purified by silica gel column chromatography to obtain the above identified compound as a colorless transparent viscous liquid (1.7 g). Refractive index $n_D^{20}$: 1.5442.

EXAMPLE 3

Preparation of 3-phenylpropyl 2-chloro-6-(4,6-dimethoxypyrimidin-2-yl)oxy benzoate (Compound No. 16)

3-phenylpropyl 6-chlorosalicylate (2.0 g), 4,6-dimethoxy-2-methysulfonylpyrimidine (1.9 g) and sodium hydrogencarbonate (0.7 g) were suspended in dimethylformamide (10 ml), and the suspension was heated and stirred at a temperature of from 100° to 120° C. for one hour. The reaction solution was poured into water and extracted with ethyl acetate. The extract was washed with water and dried. Then, the solvent was evaporated under reduced pressure. The residue thereby obtained was purified by silica gel column chromatography to obtain the above identified compound as a colorless transparent viscous liquid (2.2 g). Refractive index $n_D^{20}$: 1.5602

EXAMPLE 4

Preparation of 2-(3,5-dimethoxy)phenoxy-6-(4,6-dimethoxypyrimidin-2-yl)oxy benzoic acid (Compound No. 2-13)

10% palladium charcoal (0.5 g), methyl alcohol (150 ml) and acetic acid (10 ml) were suspended, and benzyl 2-(3,5-dimethoxy)phenoxy-6-(4,6-dimethoxypyrimidin-2-yl)oxy benzoate (5.6 g) was added thereto. The catalytic reduction was conducted under atmospheric pressure. When absorption of hydrogen terminated, the catalyst was filtered off, and the filtrate was concentrated. The residue was dissolved in ethyl ether, and the ether layer was washed with water and dried. The solvent was evaporated under reduced pressure to obtain the above identified compound as white crystals (4.0 g). Melting point: 132°–134° C.

EXAMPLE 5

Preparation of 2-(3-fluoro)phenoxy-6-(4,6-dimethoxypyrimidin-2-yl)oxy benzoic acid (Compound No. 2-27)

2-(trimethylsilyl)ethyl 2-(3-fluoro)phenoxy-6-(4,6-dimethoxypyrimidin-2-yl)oxy benzoate (4.9 g) was dissolved in dimethylformamide (30 ml). Then, tetra-n-butylammoniumfluoride (9.5 g) was added thereto, and the mixture was stirred for 15 minutes at room temperatute. The reaction solution was poured into water, and after an addition of a small amount of a saturated potassium hydrogensulfate aqueous solution, extracted with ethyl ether. The extract was washed with water and dried. Then, the solvent was evaporated under reduced pressure to obtain the above identified compound (3.5 g). Melting point: 116°–117° C.

EXAMPLE 6

Preparation of (m-tolylthio)methyl 2-chloro-6-(4,6-dimethoxypyrimidin-2-yl)oxy benzoate (Compound No. 3-4)

60% sodium hydride (0.4 g) was suspended in a 1:1 solvent mixture (40 ml) of tetrahydrofuran and dimethylformamide. Then, 2-chloro-6-(4,6-dimethoxypyrimidin-2-yl)oxy benzoic acid (3.1 g) was added thereto, and the mixture was stirred for 30 minutes. Then, (m-tolylthio)methyl chloride (1.7 g) diluted with a 1:1 solvent mixture (20 ml) of tetrahydrofuran and dimethylformamide was dropwise added at room temperature thereto, and the mixture was refluxed for 4 hours to complete the reaction.

The reaction solution was cooled to room temperature, then poured into water and extracted with toluene. The extract was washed with water and dried. Then, the solvent was evaporated under reduced pressure. The residue thereby obtained was purified by silica gel column chromatography to obtain the above identified compound as a yellow brown highly viscous substance (2.5 g). Refractive index $n_D^{20}$: 1.5923.

EXAMPLE 7

Preparation of methylsulfinylmethyl 2-chloro-6-(4,6-dimethoxypyrimidin-2-yl)oxy benzoate (Compound No. 3-1)

Methylthiomethyl 2-chloro-6-(4,6-dimethoxypyrimidin-2-yl)oxy benzoate (10.2 g) and a persulfate compound ($2KHSO_5 \cdot KHSO_4 \cdot K_2SO_4$) (40.6 g) were suspended in ethyl alcohol (100 ml), and the suspension was heated and stirred at a temperature of from 50° to 60° C. for 30 minutes to complete the reaction.

The reaction solution was poured into a large amount of water and extracted with toluene. The extract was washed with water and dried. Then, the solvent was evaporated. The residue thereby obtained was purified by silica gel column chromatography to obtain the above identified compound as a colorless transparent viscous liquid (6.0 g). Refractive index $n_D^{20}$: 1.5627.

EXAMPLE 8

Preparation of phenylthiomethyl 2-chloro-6-(4,6-dimethoxypyrimidin-2-yl)oxy benzoate (Compound No. 8)

60% NaH (1.0 g) was suspended in a solvent mixture (100 ml) of tetrahydrofuran/N,N-dimethylformamide (1/1 by volume), and 2-chloro-6-(4,6-dimethoxypyrimidin-2-yl)oxy benzoic acid (8.1 g) was added thereto. The mixture was stirred at room temperature for 0.5 hour. To this solution, chloromethylphenyl sulfide (4.1 g) was added, and the mixture was heated and stirred for 4 hours under reflux. After cooling, the mixture was poured into a large amount of water, and the resulting oily substance was extracted with toluene. The organic layer was washed with water and dried. Then, the solvent was evaporated under reduced pressure. The residue thereby obtained was crystallized from n-hexane to obtain white crystals (8.7 g). Melting point: 73.0°–75.0° C.).

EXAMPLE 9

Preparation of 2-(4,6-dimethoxypyrimidin-2-yl)oxy-6-phenoxy benzoic acid (Compound No. 2-3)

10% palladium charcoal (1.0 g), methyl alcohol (150 ml) and acetic acid (10 ml) were suspended, and then benzyl 2-(4,6-dimethoxypyrimidin-2-yl)oxy-6-phenoxy benzoate (2.8 g) was added thereto. The catalytic reduction was conducted under atmospheric pressure. When absorption of hydrogen terminated, the catalyst was filtered off, and the filtrate was concentrated to about 50 ml. The reaction solution was poured into water and extracted with ethyl ether. The ethyl ether phase was washed with a saturated sodium chloride aqueous solution and dried. Then, the solvent was evaporated under reduced pressure. The extracted crude product thus obtained was crystallized from hexane/ethanol to obtain the above identified compound as white crystals (2.0 g). Melting point: 116°–118° C.

The herbicidal composition of the present invention comprises a herbicidally effective amount of a 2-phenoxypyrimidine derivative of the present invention and an agricultural carrier or adjuvant.

When the compound of the present invention is used as a herbicide, the compound may be used as it is or as formulated in various formulations such as a wettable powder, a granule, an emulsifiable concentrate or a dust by blending it with a carrier, a surfactant, a dispersing agent or an adjuvant which is commonly employed for the formulation of agricultural chemicals.

As the carrier to be used for the formulation, there may be mentioned a solid carrier such as jeeklite, talc, bentonite, clay, kaolin, diatomaceous earth, white carbon, vermiculite, slaked lime, silica sand, ammonium sulfate or urea, or a liquid carrier such as isopropyl alcohol, xylene, cyclohexane or methyl naphthalene. As the surfactant and dispersing agent, there may be mentioned, for example, an alcohol-sulfuric acid ester, an alkyl aryl sulfonate, lignin sulfonate, a polyoxyethylene glycol ether, a polyoxyethylene alkyl aryl ether or a polyoxyethylene sorbitol mono-alkylate. As the adjuvant, for example, carboxymethyl cellulose, polyethylene glycol or gum arabic may be mentioned. In practical use, such a herbicide may be diluted to a suitable concentration before application, or may directly be applied.

The herbicide of the present invention may be used in combination with other herbicides. Examples of such other herbicides will be given below.

1-(α,α-dimethylbenzyl)-3-p-tolylurea,
2-chloro-4,6-bis(ethylamino)-1,3,5-triazine,
2-chloro-4-ethylamino-6-isopropylamino-1,3,5-triazine,
2-chloro-4,6-bis(isopropylamino)-1,3,5-triazine,
2,4-bis(ethylamino)-6-methylthio-1,3,5-triazine, 2,4-bis(isopropylamino)-6-methylthio-1,3,5-triazine,
methyl α-(4,6-dimethoxypyrimidin-2-yl carbamoyl-sulfamoyl)-O-toluylate,
1-[2-(2-chloroethoxy)phenylsulfamoyl]-3-(4-methoxy-6-methyl-1,3,5-triazin-2-yl)urea,
2-(1-ethoxyiminobutyl)-5-(2-ethylthiopropyl)-3-hydroxy-cyclohexen-2-one
methyl 3-(1-allyloxyaminobutylidene)-6,6-dimethyl-2,4-dioxocyclohexane carboxylate sodium salt,
4-(2,4-dichlorobenzoyl)-1,3-dimethyl-5-pyrazolyl-p-toluenesulfonate,
3-isopropyl-2,1,3-benzothiadiazinone-(4)-2,2-dioxide,
N-(1-ethylpropyl)-3,4-dimethyl-2,6-dinitroaniline,
α-(2-naphtoxy)propionanilide,
N-(phosphonomethyl)glycidylisopropylamine salt,
2-benzothiazol-2-yloxy-N-methylacetanilide,
2-chloro-2',6'-diethyl-N-(2-propoxyethyl)acetanilide,
2-chloro-2'-ethyl-N-(2-methoxy-1-methyl ethyl)-6'-methylacetanilide,
S-(2-methyl-1-piperidylecarbonylmethyl)-O,O-di-n-propyldithiophosphate,
2-methylthio-4-ethylamino-6-isopropylamino-1,3,5-triazine.

The herbicide of the present invention is capable of controlling various weeds in a paddy field by irrigated soil treatment before or after the emergence of weeds or by foliage treatment. Further, the herbicide is capable of controlling various weeds in an upland field by soil treatment before or after the emergence of weeds or by foliage treatment.

The dose of the active ingredient varies depending upon the field to be treated i.e. whether it is an agricultural field or non-agricultural field, the type of treatment, i.e. whether it is soil treatment or foliage treatment, the crop plants to be protected and the weeds to be killd. However, it is usually within a range of from 0.1 to 1,000 g/10 a, preferably from 0.5 to 500 g/10 a.

For instance, for soil treatment for an upland agricultural field, the dose of the active ingredient is usually from 0.5 to 500 g/10 a, although it depends on the crop plant and weeds to be killed.

For foliage treatment for an upland agricultural field, the dose is usually from 0.1 to 500 g/10 a. In the case of a non-agricultural field, the dose is usually from 1 to 1,000 g/10 a for soil or foliage treatment.

Now, Formulation Examples for the herbicidal composition of the present invention will be given. However, it should be understood that the present invention is by no means restricted to these specific Examples. In these Examples, "%" means "% by weight".

FORMULATION EXAMPLE 1 (wettable powder)

10% of Compound No. 3, 0.5% of Emulgen 810 (trademark, Kao Corporation), 0.5% of Demol N (trademark, Kao Corporation), 20% of Kunilite 201 (trademark, Kunimine Kogyo K.K.) and 69% of Jeeklite CA (tradename, Jeeklite Company Ltd.) were uniformly mixed and pulverized to obtain a wettable powder.

FORMULATION EXAMPLE 2 (emulsifiable concentrate)

30% of Compound No. 10, 20% of cyclohexanone, 11% of polyoxyethylene alkyl aryl ether, 4% of calcium alkylbenzenesulfonate and 35% of methyl naphthalene, were uniformly dissolved to obtain an emulsifiable concentrate.

FORMULATION EXAMPLE 3 (granule)

5% of Compound No. 16, 2% of a sodium salt of a lauryl alcohol-sulfuric acid ester, 5% of sodium lignin sulfonate, 2% of carboxymethyl cellulose and 86% of clay were uniformly mixed and pulverized. To 100 parts by weight of this mixture, 20 parts by weight of water was added, and the mixture was kneaded, and granulated into granules of from 14 to 32 mesh by means of an extrusion granulating machine, followed by drying to obtain granules.

FORMULATION EXAMPLE 4 (dust)

2% of Compound No. 1, 5% of diatomaceous earth and 93% of clay were uniformly mixed and pulverized to obtain a dust.

The compounds and the herbicidal compositions of the present invention are capable of effectively controlling annual weeds such as barnyardgrass (*Echinochloa crus-galli*), flatsedge (*Cyperus difformis*), monochoria (*Monochoria varinalis*), bulrush (*Scirpul hotarui*) and *Alisma canaliculatum*, and perennial weeds such as *Cyperus serotinus, Sagittaria pygmaea* and *Eleocharis kuroguwai*, grown in paddy fields. Further, they are capable of effectively controlling annual weeds such as barnyardglass (*Echinochloa crus-galli*), crabgrass (*Digitaria sanguinalis*), goosegrass (*Eleusine indica*), greenfoxtail (*Setaria viridis*), water foxtail (*Alopecurus aequalis*), annual bluegrass (*Poa annua*), wild oat (*Avena fatua*), italian ryegrass (*Lolium multiflorum*), smartweed (*Polygonum lapathifolium*), slender amaranth (*Amaranthus viridis*), lambsquarters (*Chenopodium album*), velvetleaf (*Abtilon theophrasti*), prickly sida (*Sida spinosa*), sicklepod (*Cassia tora*), chickweed (*Stellaria media*), morningglory (*Ipomoea spp*), common cocklebur (*Xanthium strumarium*), rice flatsedge (*Cyperus iria*), broadleaf signalgrass (*Brachiaria platyphylla*), itchgrass (*Rottoboellia exaltata*), downy brome (*Bromus tectorum*), wild buckwheat (*Polygonum convolvulus*), wild mustard (*Brassica arvensis*) and devils baggartickes (*Bidens frondosa*), and perennial weeds such as purple nutsedge (*Cyperus rotundus*), johnsongrass (*Sorghum halepense*), bermudagrass (*Cynodon dactylon*) and quackgrass (*Agropyron repens*) grown in upland fields. On the other hand, the safety to crop plants are extremely high. Further, the compounds of the present invention have a feature that as compared with the known compounds disclosed in the afore-mentioned publications and literature, the effects against perennial weeds such as purple nutsedge and johnsongrass are remarkably superior.

The compounds of the formula II are useful particularly as herbicides for wheat and rice plant fields, and the compounds of the formulas III and IV are useful particularly for herbicides for non-agricultural fields or for lawn and cotton fields.

Now, the herbicidal activities of the herbicides of the present invention will be described with reference to Test Examples.

TEST EXAMPLE 1 (Soil treatment)

In a 100 $cm^2$ pot filled with soil, seeds of barnyardgrass, crabgrass, smartweed, slender amarauth, lambsquater and rice flatsedge were sown and covered with soil of a thickness of from 0.5 to 1 cm. One day later from the seeding, a predetermined amount of a wettable powder prepared in accordance with Formulation Example 1, was diluted with water and applied to the soil surface at a rate of 100 liters per 10 ares (dose of active ingredient: 400 g/10 a). The evaluation was conducted on the 20th day after the treatment with the herbicide. The results were evaluated in accordance with the standards as identified in Table 4 and shown by the index numbers in Table 5-7.

TABLE 4

| Index No. | Herbicidal effects |
|---|---|
| 0 | No herbicidal effect |
| 1 | Herbicidal effect: more than 0% and less than 30% |
| 2 | Herbicidal effect: at least 30% and less than 50% |
| 3 | Herbicidal effect: at least 50% and less than 70% |
| 4 | Herbicidal effect: at least 70% and less than 90% |
| 5 | Herbicidal effect: more than 90% |

TABLE 5

| Compound No. | Herbicidal effects | | | | | |
|---|---|---|---|---|---|---|
| | Ech | Dig | Pol | Ama | Che | Cyi |
| 5 | 5 | 2 | 5 | 5 | 5 | |
| 2 | 5 | 5 | 5 | 5 | 5 | 5 |
| 3 | 5 | 5 | 5 | 5 | 5 | 5 |
| 4 | 5 | 5 | 5 | 5 | 5 | 5 |
| 5 | 5 | 5 | 5 | 5 | 5 | 5 |
| 6 | 5 | 5 | 5 | 5 | 5 | 5 |
| 7 | 5 | 3 | 5 | 5 | 5 | 4 |
| 8 | 5 | 5 | 5 | 5 | 5 | 5 |
| 9 | 5 | 5 | 5 | 5 | 5 | |
| 10 | 5 | 5 | 5 | 5 | 5 | 5 |
| 11 | 5 | 5 | 5 | 5 | 5 | 5 |
| 12 | 5 | 5 | 5 | 5 | 5 | 5 |
| 13 | 5 | 5 | 5 | 5 | 5 | 5 |
| 14 | 5 | 5 | 5 | 5 | 5 | 5 |
| 15 | 2 | 5 | 3 | 5 | 4 | 5 |
| 16 | 5 | 5 | 3 | 5 | 5 | 5 |
| 17 | 3 | 2 | 2 | 4 | 3 | 3 |
| Comparative Compound | | | | | | |
| A | 0 | 0 | 0 | 0 | 0 | 5 |
| B | 0 | 0 | 0 | 0 | 2 | 5 |
| C | 0 | 0 | 0 | 0 | 0 | 0 |

TABLE 6

| Compound No. | Herbicidal effects | | | | | |
|---|---|---|---|---|---|---|
| | Ech | Dig | Pol | Ama | Che | Cyi |
| 2-2 | 4 | 3 | 5 | 5 | 5 | 5 |
| 2-3 | 5 | 5 | 5 | 5 | 5 | 5 |
| 2-8 | 5 | 4 | 5 | 5 | 5 | 5 |
| 2-9 | 5 | 4 | 5 | 5 | 5 | 5 |
| 2-10 | 4 | 2 | 5 | 5 | 5 | 5 |
| 2-11 | 5 | 1 | 5 | 5 | 4 | 5 |
| 2-13 | 5 | 5 | 5 | 5 | 5 | 5 |
| 2-15 | 5 | 5 | 5 | 5 | 5 | 5 |
| 2-18 | 5 | 4 | 5 | 5 | 5 | 5 |
| 2-19 | 5 | 4 | 5 | 5 | 5 | 5 |
| Comparative Compound | | | | | | |
| A | 0 | 0 | 0 | 0 | 0 | 5 |
| B | 0 | 0 | 0 | 0 | 2 | 5 |
| C | 0 | 0 | 0 | 0 | 0 | 0 |

TABLE 7

| Compound No. | Herbicidal effects | | | | | |
|---|---|---|---|---|---|---|
| | Ech | Dig | Pol | Ama | Che | Cyi |
| 2-30 | 5 | 4 | 5 | 5 | 5 | 5 |
| 2-31 | 3 | 4 | 5 | 5 | 5 | 5 |
| 2-32 | 3 | 2 | 5 | 5 | 4 | 5 |
| 2-33 | 4 | 2 | 5 | 5 | 4 | 5 |
| 2-34 | 5 | 4 | 5 | 5 | 5 | 5 |
| 2-35 | 4 | 3 | 5 | 5 | 5 | 5 |
| 2-36 | 3 | 3 | 5 | 5 | 5 | 5 |
| 2-37 | 5 | 4 | 5 | 5 | 5 | 5 |
| 2-38 | 5 | 4 | 5 | 5 | 5 | 5 |
| 2-39 | 4 | 5 | 5 | 5 | 3 | 5 |
| 2-40 | 3 | 2 | 5 | 5 | 2 | 5 |
| 2-41 | 5 | 2 | 5 | 5 | 0 | 5 |
| 2-27 | 5 | 3 | 5 | 5 | 5 | 5 |
| 2-25 | 5 | 4 | 5 | 5 | 5 | 5 |

Note 1. The abbreviations of the tested plants are as follows (the same abbreviations may be used in other tables):
Ech: barnyardgrass (*Echinochloa crus-galli*)
Dig: crabgrass (*Digitaria sanguinalis*)
Pol: smartweed (*Polygonum lapathifolium*)
Ama: slender amaranth (*Amarathus viridis*)
Che: lambsquarters (*Chenopodium album*)
Cyi: rice flatsedge (*Cyperus iria*)

Note 2. Comparative Compounds A, B, and C will be identified below (the same applies in other tables): Comparative Compound A (disclosed in Japanese Unexamined Patent Publication No. 55729/1979)

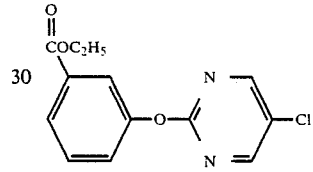

Comparative Compound B (disclosed in Japanese Unexamined Patent Publication No. 55729/1979)

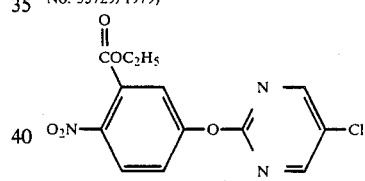

Comparative Compound C (disclosed in Arg. Biol. Chem., Vol. 30, No. 9,896 (1966))

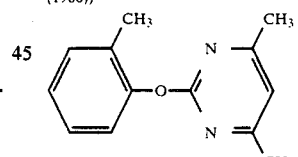

TEST EXAMPLE 2 (Soil treatment)

In a 600 cm² pot filled with soil, seeds of cotton, barnyardgrass, crabgrass, greenfoxtail, smartweed, slender amaranth and lambsquater were sown, and rhizomes of johnsongrass and tubers of purple nutsedge were planted, and covered with soil in a thickness of from 0.5 to 1 cm. One day after the seeding and plantation, a predetermined amount of a wettable powder prepared in accordance with Formulation Example 1, was diluted with water and applied to the soil surface at a rate of 100 liters per 10 ares. The evaluation was conducted on the 20th day after the treatment with the herbicides. The results were evaluated in accordance with the standard as identified as in Table 4. The results are shown by the index numbers in Table 8.

TABLE 8

| Compound No. | Dose of active ingredient (g/10a) | Phyto-toxicity Gos | Herbicidal effect | | | | | | | |
|---|---|---|---|---|---|---|---|---|---|---|
| | | | Ech | Dig | Sev | Sor | Pol | Ama | Che | Cyr |
| 3-1 | 100 | 1 | 4 | 5 | 5 | 5 | 5 | 5 | 5 | 4 |
| " | 25 | 0 | 2 | 4 | 5 | 4 | 4 | 5 | 5 | 0 |
| 3-4 | 100 | 1 | 5 | 5 | 5 | 5 | 5 | 5 | 5 | 5 |
| " | 25 | 0 | 5 | 5 | 5 | 5 | 5 | 5 | 5 | 4 |
| 3-5 | 100 | 1 | 5 | 5 | 5 | 5 | 5 | 5 | 5 | 5 |
| " | 25 | 0 | 4 | 5 | 5 | 5 | 5 | 5 | 5 | 4 |
| 3-6 | 100 | 0 | 3 | 3 | 4 | 5 | 4 | 5 | 5 | 3 |
| " | 25 | 0 | 2 | 3 | 4 | 5 | 5 | 5 | 5 | 3 |
| 3-7 | 100 | 0 | 5 | 5 | 5 | 5 | 5 | 5 | 5 | 5 |
| " | 25 | 0 | 5 | 5 | 5 | 5 | 5 | 5 | 5 | 5 |

Note:
The abbreviations of the tested plants are as follows (the same abbreviations may be used in other tables):
Gos: cotton (*Gossypium hirsutum*)
Sev: greenfoxtail (*Setaria viridis*)
Sor: johnsongrass (*Sorghum halepense*)
Cyr: purple nutdedge (*Cyperus rotundus*)

TEST EXAMPLE 3 (Foliage treatment in upland field)

In a 100 cm² pot filled with soil, seeds of barnyardgrass, crabgrass, smartweed, slender amaranth, lambsquarters and rice flatsedge, were sown and covered with soil of a thickness of from 0.5 to 1 cm. The pot was cultured in a glass chamber at a temperature of from 20° to 25° C. for 2 weeks, and then a predetermined amount of a wettable powder prepared in accordance with Formulation Example 1 was diluted with water, and applied to the foliage at a rate of 100 liters per 10 ares (dose of active ingredient: 400 g/10a). The evaluation was conducted on 14th day after the treatment with the herbicide. The results were evaluated in accordance with the standards as identified in Table 4, and shown by the index numbers in Table 9–12.

TABLE 9

| Compound No. | Herbicidal effects | | | | | |
|---|---|---|---|---|---|---|
| | Ech | Dig | Pol | Ama | Che | Cyi |
| 1 | 5 | 5 | 5 | 5 | 5 | 5 |
| 2 | 5 | 4 | 5 | 5 | 5 | 4 |
| 3 | 5 | 5 | 5 | 5 | 5 | 5 |
| 4 | 5 | 5 | 5 | 5 | 5 | 5 |
| 5 | 5 | 5 | 5 | 5 | 5 | 5 |
| 6 | 5 | 5 | 5 | 5 | 5 | 5 |
| 7 | 5 | 3 | 5 | 5 | 5 | 4 |
| 8 | 5 | 4 | 5 | 5 | 5 | 5 |
| 9 | 5 | — | 5 | 5 | 5 | 5 |
| 10 | 5 | 5 | 5 | 5 | 5 | 5 |
| 11 | 5 | 5 | 5 | 5 | 5 | 5 |
| 12 | 5 | 5 | 5 | 5 | 5 | 5 |
| 13 | 5 | 5 | 5 | 5 | 5 | 4 |
| 14 | 5 | 5 | 5 | 5 | 5 | 5 |
| 15 | 2 | 3 | 4 | 5 | 5 | 1 |
| 16 | 4 | 4 | 5 | 5 | 5 | 3 |
| 17 | 5 | 5 | 5 | 5 | 5 | 5 |
| Comparative Compound | | | | | | |
| A | 0 | 1 | 2 | 2 | 0 | 5 |
| B | 1 | 1 | 2 | 1 | 1 | 5 |
| C | 1 | 1 | 1 | 1 | 1 | 1 |

TABLE 10

| Compound No. | Herbicidal effects | | | | | |
|---|---|---|---|---|---|---|
| | Ech | Dig | Pol | Ama | Che | Cyi |
| 2-1 | 4 | 3 | 5 | 5 | 3 | 3 |
| 2-2 | 3 | — | 5 | 5 | 5 | 5 |
| 2-3 | 5 | 5 | 5 | 5 | 5 | 5 |
| 2-8 | 5 | 4 | 5 | 5 | 4 | 5 |
| 2-9 | 5 | 4 | 5 | 5 | 4 | 5 |
| 2-10 | 4 | 3 | 5 | 5 | 5 | 5 |
| 2-11 | 3 | 3 | 5 | 5 | 5 | 5 |
| 2-13 | 5 | 4 | 5 | 5 | 5 | 5 |
| 2-15 | 5 | 5 | 5 | 5 | 5 | 5 |
| 2-18 | 5 | 5 | 5 | 5 | 5 | 5 |
| 2-19 | 5 | 5 | 5 | 5 | 5 | 5 |
| 2-20 | 4 | 4 | 5 | 5 | 4 | 5 |
| 2-21 | 5 | 5 | 5 | 5 | 5 | 5 |
| 2-23 | 4 | 4 | 5 | 5 | 5 | 4 |
| 2-25 | 5 | 5 | 5 | 5 | 4 | 5 |
| 2-27 | 5 | 4 | 5 | 5 | 5 | 5 |
| 2-28 | 4 | 4 | 5 | 5 | 5 | 5 |
| 2-29 | 5 | 5 | 5 | 5 | 5 | 5 |
| Comparative Compound | | | | | | |
| A | 0 | 1 | 2 | 2 | 0 | 5 |
| B | 1 | 1 | 2 | 1 | 1 | 5 |
| C | 1 | 1 | 1 | 1 | 1 | 1 |

TABLE 11

| Compound No. | Herbicidal effects | | | | | |
|---|---|---|---|---|---|---|
| | Ech | Dig | Pol | Ama | Che | Cyi |
| 2-30 | 5 | 4 | 5 | 5 | 5 | 5 |
| 2-31 | 4 | 4 | 5 | 5 | 5 | 5 |
| 2-32 | 3 | 3 | 5 | 5 | 5 | 5 |
| 2-33 | 4 | 4 | 5 | 5 | 5 | 5 |
| 2-34 | 5 | 4 | 5 | 5 | 5 | 5 |
| 2-35 | 5 | 3 | 5 | 5 | 4 | 5 |
| 2-36 | 5 | 2 | 5 | 5 | 5 | 5 |
| 2-37 | 5 | 4 | 5 | 5 | 4 | 5 |
| 2-38 | 5 | 4 | 5 | 5 | 5 | 5 |
| 2-39 | 4 | 3 | 5 | 5 | 5 | 5 |
| 2-40 | 2 | 1 | 5 | 5 | 4 | 5 |
| 2-41 | 5 | 3 | 5 | 5 | 5 | 5 |

TABLE 12

| Compound No. | Herbicidal effects | | | | | |
|---|---|---|---|---|---|---|
| | Ech | Dig | Pol | Ama | Che | Cyi |
| 3-1 | 5 | 5 | 5 | 5 | 5 | 5 |
| 3-2 | 5 | 5 | 5 | 5 | 5 | 5 |
| 3-3 | 5 | 5 | 5 | 5 | 5 | 5 |
| 3-4 | 5 | 5 | 5 | 5 | 5 | 5 |
| 3-5 | 5 | 5 | 5 | 5 | 5 | 5 |
| 3-6 | 5 | 4 | 5 | 5 | 5 | 4 |
| 3-7 | 5 | 5 | 5 | 5 | 5 | 5 |

TABLE 12-continued

| Compound No. | Herbicidal effects | | | | | |
|---|---|---|---|---|---|---|
| | Ech | Dig | Pol | Ama | Che | Cyi |
| 3-8 | 5 | 5 | 5 | 5 | 5 | 4 |

TEST EXAMPLE 4 (Effects against perennial weeds)

In a 600 cm² pot filled with soil, tubers of purple nutsedge and rhizomes of johnsongrass were planted and covered with soil of a thickness of from 0.5 to 1 cm. For the soil treatment, a predetermined amount of a wettable powder prepared in accordance with Formulation Example 1 was diluted with water and applied to the soil surface at a rate of 100 liters per 10 ares one day after the plantation. For the foliage treatment, the pot was cultured in a glass chamber at a temperature of from 20° to 25° C. for 2 weeks, and then a predetermined amount of a wettable powder prepared in accordance with Formulation Example 1 was diluted with water containing 2,000 ppm of surfactant wk as an extender and applied to the foliage at a rate of 100 liters per 10 ares. The evaluation was conducted on the 30th day after the treatment with the herbicide in the case of the soil treatment, and on the 21st day in the case of the foliage treatment. The results were evaluated in accordance with the standards as identified in Table 4 and shown by the index numbers in Table 13-18.

TABLE 13

| Compound No. | Dose of active ingredient (g/10a) | Soil Treatment | |
|---|---|---|---|
| | | Cyr | Sor |
| 2 | 400 | 5 | 5 |
| 3 | 400 | 5 | 5 |
| 4 | 400 | 5 | — |
| 5 | 400 | 5 | 5 |
| 6 | 400 | 2 | 5 |
| 8 | 400 | 4 | 5 |
| 9 | 400 | 2 | 5 |
| 11 | 400 | 4 | — |
| 12 | 400 | 5 | — |
| 13 | 400 | 4 | — |
| 14 | 400 | 5 | — |
| Comparative Compound | | | |
| A | 400 | 0 | 0 |
| B | 400 | 0 | 0 |
| C | 400 | 0 | 0 |
| D | 400 | 1 | 0 |

Note: The Comparative compound D is as follows (the same compound may be used in other tables):

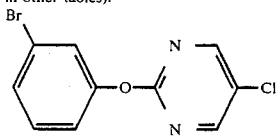

TABLE 14

| Compound No. | Dose of active ingredient (g/10a) | Foliage Treatment | |
|---|---|---|---|
| | | Cyr | Sor |
| 2 | 400 | 5 | — |
| 3 | 400 | 5 | — |
| 4 | 400 | 5 | — |
| 5 | 400 | 5 | — |
| 6 | 400 | 5 | — |
| 8 | 400 | 5 | — |

TABLE 14-continued

| | Dose of active ingredient (g/10a) | Foliage Treatment | |
|---|---|---|---|
| | | Cyr | Sor |
| 9 | 400 | 4 | — |
| 10 | 400 | 5 | — |
| 11 | 400 | 5 | — |
| 12 | 400 | 5 | — |
| 13 | 400 | 5 | — |
| 14 | 400 | 5 | — |
| 17 | 400 | 5 | 5 |
| Comparative Compound | | | |
| A | 400 | 0 | 0 |
| B | 400 | 0 | 0 |
| C | 400 | 0 | 0 |
| D | 400 | 1 | 1 |

TABLE 15

| Compound No. | Dose of active ingredient (g/10a) | Soil Treatment Cyr |
|---|---|---|
| 2-2 | 400 | 5 |
| 2-3 | 400 | 5 |
| 2-8 | 400 | 5 |
| 2-9 | 400 | 5 |
| 2-10 | 400 | 5 |
| 2-13 | 400 | 5 |
| 2-15 | 400 | 5 |
| 2-18 | 400 | 5 |
| 2-19 | 400 | 5 |
| 2-20 | 400 | 5 |
| Comparative Compound | | |
| A | 400 | 0 |
| B | 400 | 0 |
| C | 400 | 0 |
| D | 400 | 1 |

TABLE 16

| Compound No. | Dose of active ingredient (g/10a) | Foliage Treatment | |
|---|---|---|---|
| | | Cyr | Sor |
| 2-3 | 400 | 5 | 5 |
| 2-8 | 400 | 5 | — |
| 2-9 | 400 | 5 | — |
| 2-10 | 400 | 5 | — |
| 2-13 | 400 | 5 | — |
| 2-15 | 400 | 5 | — |
| 2-18 | 400 | 5 | — |
| 2-19 | 400 | 5 | — |
| 2-20 | 400 | 5 | — |
| 2-21 | 400 | 4 | — |
| Comparative Compound | | | |
| A | 400 | 0 | 0 |
| B | 400 | 0 | 0 |
| C | 400 | 0 | 0 |
| D | 400 | 1 | 1 |

TABLE 17

| Compound No. | Dose of active ingredient (g/10a) | Soil Treatment Cyr |
|---|---|---|
| 2-30 | 100 | 5 |
| 2-31 | 100 | 5 |
| 2-40 | 100 | 5 |
| 2-41 | 100 | 5 |
| 2-4 | 400 | 4 |

TABLE 17-continued

| Compound No. | Dose of active ingredient (g/10a) | Soil Treatment Cyr |
|---|---|---|
| 2-27 | 100 | 5 |

TABLE 18

| Compound No. | Dose of active ingredient (g/10a) | Foliage Treatment Cyr |
|---|---|---|
| 2-31 | 100 | 4 |
| 2-32 | 100 | 5 |
| 2-33 | 100 | 5 |
| 2-38 | 100 | 5 |
| 2-39 | 100 | 4 |
| 2-40 | 100 | 4 |
| 2-25 | 400 | 4 |
| 2-27 | 100 | 5 |

TEST EXAMPLE 5 (Safety to crop plants)

In 600 cm² pots filled with soil, seeds of barnyardgrass, greenfoxtail, smartweed, slender amaranth, water foxtail, lambsquarters, soybean, cotton and wheat were sown tubers of purple nutsedge and rhizomes of johnsongrass were planted, and they were covered with soil of a thickness of from 0.5 to 1 cm. For the soil treatment, a predetermined amount of a wettable powder prepared in accordance with Formulation Example 8 was diluted with water and applied to the soil surface at a rate of 100 liters per 10 ares one day after the plantation. For the foliage treatment, the pot was cultured in a greenhouse for about 3 weeks, and then a predetermined amount of a wettable powder prepared in accordance with Formulation Example 8 was diluted with water and applied to the foliage at a rate of 100 liters per 10 ares. The evaluation was conducted on the 30th day after the treatment with the herbicide in the case of the soil treatment, and on the 30th day in the case of the foliage treatment. The evaluation of the herbicidal effects was conducted in accordance with the standards as identified in Table 4, and the evaluation of phytotoxicity was conducted in accordance with the standards as identified in Table 19. The results are shown by the index numbers in Tables 20.

TABLE 19

| Index | Phytotoxicity |
|---|---|
| 0 | No phytotoxicity |
| 1 | Phytotoxicity more than 0% and less than 30% |
| 2 | Phytotoxicity at least 30% and less than 50% |
| 3 | Phytotoxicity at least 50% and less than 70% |
| 4 | Phytotoxicity at least 70% and less than 90% |
| 5 | Phytotoxicity at least 90% to completely withered |

TABLE 20

| Compound No. | Dose of active ingredient (g/10a) | Phyto-toxicity Gos | Herbicidal effect Ech | Pol | Sor |
|---|---|---|---|---|---|
| 2 | 25 | 0 | 4 | 5 | 5 |
| 4 | 6.3 | 1 | 5 | 5 | 4 |
| 5 | 25 | 0 | 5 | 5 | 5 |
| 6 | 100 | 1 | 4 | 5 | 5 |
| 8 | 100 | 0 | 5 | 5 | 5 |
| 9 | 100 | 1 | 5 | 5 | 5 |
| 10 | 25 | 2 | 5 | 5 | 5 |
| Comparative compound | | | | | |
| A | 100 | 0 | 0 | 0 | 0 |
| B | 100 | 0 | 0 | 0 | 0 |
| C | 100 | 0 | 0 | 0 | 0 |

TEST EXAMPLE 6 (Safety to crop plants)

In a 100 cm² pot filled with soil, seeds of smartweed, slender amaranth, lambsquaters and wheat were sown and covered with soil of a thickness of from 0.5 to 1 cm. One day after the seeding, a wettable powder prepared in accordance with Formulation Example 1 was diluted with water and applied to the soil surface at a rate of 100 liters per 10 ares so that 6.3 g of the active ingredient per 10 ares would be applied. The evaluation was conducted on the 30th day after the treatment with the herbicide. The evaluation of the herbicidal effects was conducted in accordance with the standard as identified in Table 4, and the evaluation of phytotoxicity was conducted in accordance with the standard as identified in Table 19. The results are shown by the index numbers in Tables 21 and 22.

TABLE 21

(Soil treatment effects)

| Compound No. | Phyto-toxicity Tri | Herbicidal effect Ech | Pol | Che |
|---|---|---|---|---|
| 2-3 | 0 | 5 | 5 | 5 |
| 2-8 | 0 | 5 | 5 | 5 |
| 2-9 | 0 | 5 | 5 | 5 |
| 2-13 | 0 | 2 | 5 | 5 |
| 2-15 | 0 | 3 | 4 | 5 |
| 2-19 | 0 | 5 | 5 | 5 |
| Comparative compound | | | | |
| D | 0 | 0 | 0 | 0 |

Note:
The abbreviation of the tested plant is as follows (the same abbreviation may be used in other tables):
Tri: Wheat (*Triticum aestivum*)

TABLE 22

| Compound No. | Phyto-toxicity Tri | Herbicidal effect Pol | Ama | Che |
|---|---|---|---|---|
| 2-40 | 1 | 5 | 5 | 5 |

TEST EXAMPLE 7 (Safety to crop plants)

In a 100 cm² pot filled with soil, seeds of smartweed, slender amaranth, wild radish and wheat were sown and covered with soil of a thickness of from 0.5 to 1 cm. The pot was cultured in a grass chamber at a temperature of from 20° to 25° C. for two weeks, and then a predetermined amount of a wettable powder prepared in accordance with Formulation Example 1 was diluted with water containing 200 ppm of surfactant wk and applied to the foliage at a rate of 100 liters per 10 ares.

The evaluation was conducted on the 21st day. The results were evaluated in accordance with the standards as identified in Tables 4 and 18 and shown by the index numbers in Tables 23 and 24.

TABLE 23

(Foliage treatment effects)

| Compound No. | Dose of active ingredient (g/10a) | Phyto-toxicity Tri | Herbicidal effect Pol | Ama | Rap |
|---|---|---|---|---|---|
| 2-3 | 1 | 1 | 5 | 5 | 5 |
| 2-8 | 3 | 1 | 4 | 4 | 5 |
| 2-9 | 3 | 0 | 5 | 5 | 5 |
| 2-10 | 3 | 0 | 4 | 5 | 5 |
| 2-13 | 1.6 | 0 | 4 | 5 | 5 |
| Comparative compound D | 0 | 0 | 0 | 0 | |

Note:
The abbreviation of the tested plant is as follows (the same abbreviation may be used in other tables):
Rap: Wild radish (*Raphanus raphanistrum*)

TABLE 24

| Compound No. | Dose of active ingredient (g/10a) | Phyto-toxicity Tri | Herbicidal effect Pol | Ama |
|---|---|---|---|---|
| 2-31 | 25 | 0 | 5 | 5 |
| 2-32 | 25 | 0 | 5 | 5 |
| 2-33 | 25 | 0 | 5 | 5 |
| 2-38 | 25 | 1 | 5 | 5 |
| 2-39 | 25 | 0 | 5 | 5 |
| 2-40 | 25 | 0 | 5 | 5 |

TEST EXAMPLE 8 (Herbicidal effects against paddy field weeds)

In a 100 cm² pot, paddy field soil was filled and paddled, seeds of barnyardgrass, unbrellaplant, monochoria and bulrush were sown. Then, water was introduced to a depth of 5 cm. Two days after the seeding, a wettable powder prepared in accordance with Formulation Example 1 was diluted with water and dropwise added to the water surface so that 100 g of the active ingredient per 10 ares was applied. The evaluation was conducted on the 21st day after the application in accordance with the standards as identified in Table 4. The results are shown by the index numbers in Tables 25 and 26.

TABLE 25

| | Herbicidal effects | | | |
|---|---|---|---|---|
| | Ech | Cyp | Mon | Sci |
| Compound No. | | | | |
| 2-1 | 5 | 5 | 5 | 2 |
| 2-2 | 5 | 5 | 5 | 5 |
| 2-3 | 5 | 5 | 5 | 5 |
| 2-4 | 4 | 5 | 5 | 4 |
| 2-5 | 4 | 5 | 5 | 4 |
| 2-6 | 3 | 2 | 5 | 2 |
| 2-8 | 5 | 5 | 5 | 5 |
| 2-9 | 5 | 5 | 5 | 5 |
| 2-10 | 4 | 5 | 5 | 5 |
| 2-11 | 4 | 5 | 5 | 5 |
| 2-13 | 5 | 5 | 5 | 5 |
| 2-14 | 4 | 2 | 5 | 3 |
| 2-15 | 5 | 5 | 5 | 5 |

TABLE 25-continued

| | Herbicidal effects | | | |
|---|---|---|---|---|
| | Ech | Cyp | Mon | Sci |
| 2-16 | 3 | 4 | 5 | 4 |
| 2-18 | 5 | 5 | 5 | 5 |
| 2-19 | 5 | 5 | 5 | 5 |
| 2-20 | 5 | 5 | 5 | 5 |
| 2-21 | 5 | 5 | 5 | 5 |
| 2-22 | 5 | 5 | 5 | 5 |
| 2-23 | 5 | 5 | 5 | 5 |
| 2-24 | 5 | 5 | 5 | 5 |
| 2-25 | 5 | 5 | 5 | 5 |
| 2-26 | 4 | 5 | 5 | 5 |
| Comparative Compound | | | | |
| A | 0 | 3 | 0 | 1 |
| B | 0 | 5 | 0 | 1 |
| C | 0 | 0 | 0 | 0 |

TABLE 26

| Compound No. | Herbicidal effects | | | |
|---|---|---|---|---|
| | Ech | Cyp | Mon | Sci |
| 2-30 | 5 | 5 | 5 | 5 |
| 2-31 | 5 | 5 | 5 | 5 |
| 2-32 | 4 | 5 | 5 | 5 |
| 2-33 | 3 | 5 | 5 | 5 |
| 2-34 | 5 | 5 | 5 | 5 |
| 2-35 | 5 | 5 | 5 | 5 |
| 2-36 | 5 | 5 | 5 | 5 |
| 2-37 | 5 | 5 | 5 | 5 |
| 2-38 | 5 | 5 | 5 | 5 |
| 2-39 | 5 | 5 | 5 | 5 |
| 2-40 | 4 | 5 | 5 | 5 |
| 2-41 | 5 | 5 | 5 | 5 |

TEST EXAMPLE 9 (Herbicidal effects against paddy field weeds)

In a 100 cm² pot, paddy field soil was filled and paddled, seeds of barnyardgrass, unbrellaplant, monochoria and bulrush were sown. Then, water was introduced to a depth of 5 cm. Two days after the seeding, a wettable powder prepared in accordance with Formulation Example 1 was diluted with water and dropwise added to the water surface so that 100 g of the active ingredient per 10 ares was applied. The evaluation was conducted on the 21st day after the application in accordance with the standards as identified in Table 4. The results are shown by the index numbers in Table 27.

TABLE 27

| Compound No. | Herbicidal effects | | | |
|---|---|---|---|---|
| | Ech | Cyp | Mon | Sci |
| 3-1 | 5 | 5 | 5 | 5 |
| 3-2 | 5 | 5 | 5 | 5 |
| 3-3 | 5 | 5 | 5 | 5 |
| 3-4 | 5 | 5 | 5 | 5 |
| 3-5 | 5 | 5 | 5 | 5 |
| 3-6 | 5 | 4 | 5 | 4 |
| 3-7 | 5 | 5 | 5 | 5 |
| 3-8 | 5 | 5 | 5 | 5 |

We claim:

1. A 2-phenoxypyrimidide derivative having the formula:

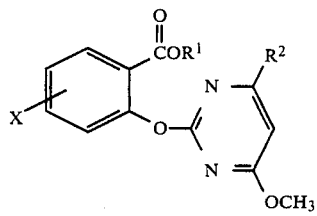

wherein X is a group of the formula:

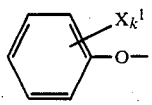

wherein $X^1$ is a halogen atom, a lower alkyl group, a lower alkoxy group, a nitro group or a lower alkylthio group and k is 0, 1 or 2; $R^1$ is a hydrogen atom, a benzyl group or a group of the formula $-(CH_2)_m R^3$, wherein $R^3$ is a cyano group, a formyl group, a lower dialkylamino group, a phenyl group, a pyridyl group, a trimethylsilyl group, a naphthyl group, a lower alkoxycarbonyl group, a benzoyl group, a lower alkylthio group, a phenylthio group, a lower alkylsulfonyl group or a benzyloxy group and m is 1, 2 or 3, or a group of the formula:

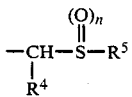

wherein $R^4$ is a hydrogen atom or a lower alkyl group, $R^5$ is a lower alkyl group or a group of the formula:

wherein $X^2$ is a hydrogen atom, a halogen atom, a lower alkyl group, a lower alkoxy group or a nitro group, and n is 0 or 1; provided that when $R^5$ is a lower alkyl group, n is 1; and $R^2$ is a chlorine atom or a methoxy group.

2. A 2-phenoxypyrimidine derivative having the formula:

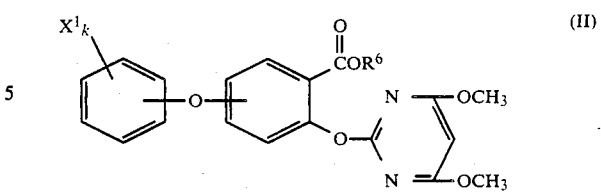

wherein $X^1$ is a halogen atom, a lower alkyl group or a lower alkoxy group, k is 0, 1 or 2, and $R^6$ is a hydrogen atom or a benzyl group.

3. The compound according to the claim 2, wherein $X^1$ is a methyl group, a methoxy group or a halogen atom, and k is 1 or 2.

4. The compound according to claim 2, wherein the phenoxy group is at the 5-position or at the 6-position.

5. The compound according to claim 2, wherein k is 0 or $R^6$ is a hydrogen atom or both.

6. The compound according to claim 1, wherein $R^2$ is a methoxy group.

7. The compound according to claim 1, wherein $R^2$ is a methoxy group, and $R^3$ is a benzoyl group, a benzyloxy group, an alkylthio group, an alkoxycarbonyl group, a phenylthio group, an alkylsulfonyl group or a cyano group.

8. The compound according to claim 1, wherein $R^2$ is a methoxy group, and $R^3$ is a benzyloxy group, an alkylthio group, a phenylthio group or an alkylsulfonyl group, and m is 1.

9. The compound according to claim 1, wherein n is 0 and $R^5$ is

10. The compound according to claim 1, wherein n is 0 and $R^5$ is

wherein $X^4$ is a hydrogen atom, a methyl group, a methoxy group or a nitro group.

11. A herbicidal composition which comprises a herbicidally effective amount of a 2-phenoxypyrimidine derivative of the formula I as defined in claim 1 and an agricultural adjuvant.

* * * * *